United States Patent
Choi et al.

(10) Patent No.: US 10,752,638 B2
(45) Date of Patent: Aug. 25, 2020

(54) METHOD FOR PRODUCING ANHYDROSUGAR ALCOHOL BY HIGH-PRESSURE REACTION

(71) Applicant: SK Innovation Co., Ltd., Seoul (KR)

(72) Inventors: Young Bo Choi, Seoul (KR); Sang Il Lee, Daejeon (KR); Sung Real Son, Daejeon (KR); In Hyoup Song, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 16/385,414

(22) Filed: Apr. 16, 2019

(65) Prior Publication Data

US 2019/0241581 A1 Aug. 8, 2019

Related U.S. Application Data

(63) Continuation-in-part of application No. 15/518,800, filed as application No. PCT/KR2015/010585 on Oct. 7, 2015, now abandoned.

(30) Foreign Application Priority Data

Oct. 16, 2014 (KR) .................. 10-2014-0139662

(51) Int. Cl.
*C07D 493/04* (2006.01)
*C07H 1/00* (2006.01)

(52) U.S. Cl.
CPC ............. *C07D 493/04* (2013.01); *C07H 1/00* (2013.01)

(58) Field of Classification Search
CPC ................................ C07D 493/04; C07H 1/00
See application file for complete search history.

(56) References Cited

U.S. PATENT DOCUMENTS

| | | | |
|---|---|---|---|
| 2,735,792 A | 2/1956 | Kroyer | |
| 6,013,812 A | 1/2000 | Haas et al. | |
| 6,639,067 B1 | 10/2003 | Brinegar et al. | |
| 7,420,067 B2 | 9/2008 | Sanborn | |
| 8,617,418 B2 | 12/2013 | Sekiguchi et al. | |
| 9,169,263 B1 | 10/2015 | Ryu et al. | |
| 2007/0213544 A1 | 9/2007 | Sanborn | |
| 2009/0259057 A1 | 10/2009 | Schreck et al. | |
| 2014/0088315 A1 | 3/2014 | Ryu | |
| 2017/0240559 A1* | 8/2017 | Choi | .................... C07D 493/04 |

FOREIGN PATENT DOCUMENTS

| | | |
|---|---|---|
| KR | 20010079763 A | 8/2001 |
| KR | 1020090132933 | 7/2011 |
| KR | 1020120114051 | 4/2014 |
| KR | 1020140059902 A | 5/2014 |
| KR | 1020140105189 A | 9/2014 |

OTHER PUBLICATIONS

Boiling Point Caculator (http://www.trimen.pl/witek/calculations/wrzenie.html) access online Jan. 4, 2019.
Huang et al.; "Catalytic Depolymerization of Lignin in Supercritical Ethanol"; ChemSusChem; 2014; pp. 2276-2288; vol. 7.
Myers, "What is the boiling point and heat vaporization of sulfuric acid?", Journal of Chemical Education 60.12, 1983, 1017.
Sauer, "Tubular plug flow reactors", Ullman's Encyclopedia of Industrial Chemistry, 2013, p. 1-23.
Williams, "pKa data compiled by R." Williams. Dostopno na svetovnem slpetu: http://research.chem.psu.edu/orpgroup/pKa_compilation.pdf (Mar. 5, 2013), 2004.

* cited by examiner

*Primary Examiner* — John M Mauro
(74) *Attorney, Agent, or Firm* — The Webb Law Firm

(57) ABSTRACT

The present invention relates to a method of producing anhydrosugar alcohol by dehydrating sugar alcohol at high pressure in the presence of a catalyst which is less acidic than a conventional sulfuric acid catalyst and which can suppress side reactions at high temperature. According to the present invention, anhydrosugar alcohol can be produced in a yield similar to that in a vacuum reaction.

15 Claims, No Drawings

METHOD FOR PRODUCING ANHYDROSUGAR ALCOHOL BY HIGH-PRESSURE REACTION

CROSS-REFERENCE TO RELATED APPLICATIONS

This application is a continuation-in-part of U.S. patent application Ser. No. 15/518,800, filed Apr. 13, 2017, which is the national phase of International Application No. PCT/KR2015/010585 filed Oct. 7, 2015, and claims priority to Korean Patent Application No. 10-2014-0139662 filed Oct. 16, 2014, the disclosures of which are hereby incorporated in their entirety by reference.

TECHNICAL FIELD

The present invention relates to a method of preparing anhydrosugar alcohol, and more particularly to a method of producing anhydrosugar alcohol by dehydrating sugar alcohol at high pressure in the presence of a catalyst which is less acidic than a conventional sulfuric acid catalyst and which can suppress side reactions at high temperature.

BACKGROUND ART

Due to the exhaustion of traditional energy sources together with an increase in the global energy demand, impetus is currently being given to the development of alternative energy sources. Among them, biomass is renewable quantitative biological resource that attracts a great deal of attention.

Among biomass-based industrial raw materials, isosorbide ($C_6H_{10}O_4$) that is prepared by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide may be used as an additive that can make plastic materials stronger and tougher, and that is also used as an agent for treating cardiac diseases by being boded to nitrate.

When D-glucose obtained from biomass by pretreatment is hydrogenated in the presence of a catalyst, sorbitol is produced. Isosorbide is produced by double dehydration of sorbitol. This cyclization reaction is influenced by various reaction conditions, including temperature, pressure, solvent, catalyst, etc.

Currently, as a method of preparing isosorbide from sorbitol, a process is widely used in which sulfuric acid is used as a catalyst and a reaction is carried out under a reduced pressure of about 10 mmHg. However, when a liquid strong acid catalyst such as sulfuric acid is used, a reactor is easily corroded, and for this reason, an expensive reactor should be used. In addition, a large amount of energy is continuously consumed to maintain a high vacuum level of about 10 mmHg, and thus the operating cost for the reaction is high, and high-reliability continuous vacuum reactor is also not easy to manufacture.

In recent years, in an attempt to solve the problems of such vacuum reactions, methods of carrying out reactions under high-temperature and high-pressure conditions have been reported.

U.S. Pat. No. 7,420,067 discloses a process for producing anhydrosugar alcohol, comprising: heating sugar alcohol or monoanhydrosugar alcohol to a temperature of 150° C. to 350° C. in the presence of an acidic catalyst; and pressurizing the sugar alcohol or monoanhydrosugar alcohol to a pressure of 130 psi to 2000 psi. U.S. Pat. No. 6,013,812 discloses a process for producing anhydrosugar alcohol, comprising reacting a polyol in the presence of an acidic catalyst and a hydrogenating catalyst at a temperature of at least 100° C. and a hydrogen pressure of 1 MPa to 20 MPa. These high-pressure reactions aim to increase isosorbide purity rather than the yield of isosorbide, and have a disadvantage in that the yield of isosorbide is lower than that in the vacuum reactions. U.S. Pat. No. 7,420,067 shows a yield of 41.4 mol % to 59.8 mol %, and U.S. Pat. No. 6,013,812 shows a yield of up to 46 mol %.

Meanwhile, the cost of the raw material sorbitol accounts for about 50% or more of the total production cost of isosorbide. For this reason, in order for the high-pressure reaction to be used commercially, the high-pressure reaction is required to have a yield similar to that of the vacuum reaction.

Accordingly, the present inventors have found that, when an effective catalyst, which is less acidic than sulfuric acid and can suppress side reactions at high temperature, is selected and used in a high-pressure reaction that converts sorbitol to isosorbide, the yield of isosorbide in the high-pressure reaction can be increased to a level similar to that in a vacuum reaction, thereby completing the present invention.

SUMMARY OF INVENTION

It is an object of the present invention to provide a method of preparing anhydrosugar alcohol, which can increase the yield of anhydrosugar alcohol in a high-pressure reaction that converts sugar alcohol to anhydrosugar alcohol by dehydration.

DETAILED DESCRIPTION OF THE INVENTION

To achieve the above object, the present invention provides method of preparing anhydrosugar alcohol, the method comprises: dehydrating a sugar alcohol at a pressure of 10 bar to 50 bar in the presence of a catalyst having the following properties:
 (a) a boiling point of 160° C. or higher at 10 mmHg;
 (b) an acidity of $-3.0 < pK_a < 3.0$; and
 (c) reacting in a homogeneous phase.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

The reason why a vacuum reaction is applied to a reaction that converts sorbitol to isosorbide by dehydration is to continuously remove water from the reactant, because water molecules resulting from dehydration reduce the concentration of a catalyst and interfere with the reaction. Thus, when the reaction is carried out at a vacuum level of about 10 mmHg in the presence of sulfuric acid, the reaction can be carried out even at a low temperature of about 120 to 140° C., because the amount of water that interferes with the reaction is small. On the other hand, a high-pressure reaction in which water is not removed requires a higher reaction temperature even in the presence of the same catalyst as used in the vacuum reaction, because the amount of water (that interferes with the reaction) in the high-pressure reaction is larger than that in the vacuum reaction. However, when the reaction temperature is increased, the amount of side reactions, such as decomposition, polymerization and char formation, will increase. Particularly, when a strong acid catalyst such as sulfuric acid is used, a large amount of side reactions will occur at high temperature.

Thus, it is important to select an effective catalyst which is less acidic than sulfuric acid and which can suppress side reactions at high temperature.

In the present invention, the yield of isosorbide in a dehydration reaction that converts sorbitol to isosorbide under the high-temperature and high-pressure conditions of temperature of 160° C. to 260° C. and pressure of 10 bar to 50 bar could be increased by using a catalyst which has a boiling point higher than that of isosorbide so as to maintain its activity without evaporation during the reaction and which can be easily separated from isosorbide in a purification process such as vacuum distillation and which reacts in a homogeneous phase under the reaction conditions to increase the efficiency of contact between the catalyst and the feed and which has an acidity suitable for reducing the production of by-products such as a polymers or cokes at high reaction temperature.

Therefore, in one aspect, the present invention is directed to method of preparing anhydrosugar alcohol, the method comprises: dehydrating a sugar alcohol at a pressure of 10 bar to 50 bar in the presence of a catalyst having the following properties:
(a) a boiling point of 160° C. or higher at 10 mmHg;
(b) an acidity of $-3.0 < pK_a < 3.0$; and
(c) reacting in a homogeneous phase.

The catalyst that is used in the present invention satisfies the following conditions:
(a) Boiling Point A catalyst having a boiling point higher than the boiling point of isosorbide (160° C. at 10 mmHg) is selected in order to maintain the activity of the catalyst without evaporation of the catalyst during the reaction and to easily separate the catalyst from isosorbide in a purification process such as vacuum distillation. Namely, the selected catalyst has a boiling point of 160° C. or higher at 10 mmHg.

(b) Acidity ($pK_a$)

The catalyst that is used in the present invention has an acidity suitable for reducing the production of by-products, such as polymers or cokes, at high reaction temperature. To increase the yield of isosorbide, the catalyst may have a pKa of $-3.0 < pK_a < 3.0$, preferably $-2.0 < pK_a < 2.5$, more preferably $-1.0 < pK_a < 1.9$.

(3) Homogeneous Phase

The catalyst that is used in the present invention, which reacts in a homogeneous phase under reaction conditions to increase the efficiency of contact between the catalyst and the feed. To this end, the catalyst may have a melting point of 180° C. or lower, preferably 160° C. or lower, more preferably 140° C. or lower, particularly preferably 120° C. or lower.

An embodiment of the present invention provides a method of preparing anhydrosugar alcohol, the method comprises: dehydrating a sugar alcohol at a pressure of 10 bar to 50 bar in a presence of a catalyst having:
(a) a boiling point of 160° C. or higher at 10 mmHg;
(b) an acidity of $-3.0 < pK_a < 1.9$; and
(c) reacting in a homogeneous phase,
wherein the catalyst is at least one selected from the group consisting of naphthalenesulfonic acid, methansulfonic acid and p-tolunesulfonic acid.

The catalyst used in the present invention may be at least one selected from the group consisting of naphthalenesulfonic acid, methansulfonic acid and p-tolunesulfonic acid, and preferably the catalyst may be naphthalenesulfonic acid. Specific examples of naphthalenesulfonic acid include 2-naphthalenesulfonic acid and 1-naphthalenesulfonic acid, which are isomers produced by sulfonation of naphthalene. 2-naphthalenesulfonic acid satisfies the following conditions: $pK_a=0.27$, m.p.=91° C., and b.p.=391.6° C. (having a boiling point of 160° C. or higher at 10 mmHg), and 1-naphthalenesulfonic acid satisfies the following conditions: $pK_a=0.17$, m.p.=90° C., and b.p.=392° C.

The temperature of the reaction may range from 160° C. to 260° C., preferably from 190° C. to 230° C. If temperature of the reaction is lower than 160° C., the reaction time or the residence time will be very long, and if the temperature of the reaction is higher than 260° C., side reactions can be promoted to reduce the yield of isosorbide.

The pressure of the reaction may range from 10 bar to 50 bar, preferably from 15 bar to 40 bar. Although the pressure of the reaction may also be artificially generated using an inert gas such as nitrogen or helium, the reaction may preferably be performed using an autogeneous pressure or a self-generated pressure which is generated by a solvent (e.g., water, ethanol or a mixture thereof) containing a sugar alcohol solution when gas-liquid equilibrium is reached at the reaction pressure. When the autogeneous or self-generated pressure is used, the reaction may be performed at a pressure which is generated during heating to the reaction temperature after 50-90% (preferably 60-80%) of the reactor volume is filled with the reactant.

In view of process efficiency, cost effectiveness increases as the amount of catalyst added decreases. The catalyst that is used in the present invention may be added in an amount of 0.1-5 parts by mole, preferably 0.5-3 parts by mole, based on 100 parts by mole of sugar alcohol. If the catalyst is added in an amount of less than 0.1 parts by mole, there will be a problem in that the dehydration reaction is very time-consuming, and if the catalyst is added in an amount of more than 5 moles by part, there will be a problem in that the production of sugar polymers as by-products increase to reduce the yield of isosorbide.

In the present invention, the sugar alcohol may be hexitol. Specifically, it may be one or more selected from the group consisting of sorbitol, mannitol and iditol. Preferably, the sugar alcohol is sorbitol. The anhydrosugar alcohol may be isosorbide, isomannide, isoidide or the like. Preferably, the anhydrosugar alcohol is isosorbide.

The method of preparing anhydrosugar alcohol according to the present invention may be performed in a batch or continuous manner. It may be performed in a continuous stirred tank reactor (CSTR), a plug flow reactor (PFR) or a batch reactor (BR).

In a high-temperature hydrothermal reaction, carbonized material resulting from carbonization of a reactant, an intermediate or polymer by-products is formed in an amount of about 10 wt % or more and is adsorbed mainly onto the reactor wall surface and the impeller surface. When the formation of such carbonized material is inhibited, a scale-up and continuous process will be more advantageously applied. It is believed that the carbonized material is formed by a polymerization or char reaction. Meanwhile, when ethanol used as a solvent is heated to a temperature of 160° C. to 260° C. so as to generate autogenous pressure, it will have the properties of a supercritical or subcritical fluid. In addition, ethanol which is in a supercritical or subcritical state has an advantage in that it can decompose char while inhibiting the formation of char from lignin (DOI: 10.1002/cssc.201402094, Catalytic Depolymerization of Lignin in Supercritical Ethanol, ChemSusChem). The method of preparing isosorbide according to the present invention is performed under the temperature and pressure conditions similar to those in which supercritical/subcritical ethanol is formed. Thus, when ethanol is used as a reaction solvent in the method of the present invention, char formation can be prevented.

In addition, the method of preparing anhydrosugar alcohol according to the present invention may further comprise, after producing the anhydrosugar alcohol, a step of separating and/or purifying the product. The step of separating and/or purifying the product may be performed using distillation, crystallization and adsorption processes alone or in combination of two or more.

Meanwhile, for separation and purification of the product, it is required to remove water, ethanol or a mixture thereof used as a solvent for the reactant. For this removal of water, ethanol or a mixture thereof, a large amount of energy is required. In the method of preparing isosorbide according to the present invention, solvent can be removed without having to use energy, because water or ethanol having a boiling point lower than that of sugar alcohol or anhydrosugar alcohol is easily evaporated when the pressure of the reactor is reduced to atmospheric pressure after completion of the reaction which is performed at a pressure of 10-50 bar. Thus, the method of the present invention is very excellent in terms of energy efficiency and cost effectiveness.

The amount of water which can be removed through a reduced-pressure process and the amount of energy which is used for this removal can be controlled by controlling the temperature of the reduced-pressure process. For example, when the pressure of the reaction is merely reduced to atmospheric pressure without using additional energy, about 40-80% of water can be removed. In addition, when a small amount of heat is supplied, 70-100% of water can be removed. Thus, the method of preparing isosorbide according to the present invention has an advantage in that water can be removed in an economic manner.

Meanwhile, a conventional method that uses a strong acid catalyst further comprises, before distillation, a step of adding an alkali to a dehydration reaction product to neutralize the reaction product, whereas the method of preparing anhydrosugar alcohol according to the present invention does not require the neutralizing step.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

90 g of a 70 wt % aqueous solution of D-sorbitol (Aldrich), which contains 63 g (0.3458 mol) of D-sorbitol, and 3.025 mmol (0.875 parts by mole based on 100 parts by mole of D-sorbitol contained in the reactant) of a naphthalenesulfonic acid catalyst, were introduced into an autoclave reactor and allowed to react with stirring at 180° C. for 8 hours. Because the reaction pressure used was autogenous pressure, the reaction pressure was somewhat different between the initial stage of the reaction and the end stage of the reaction depending to the degree of progress of the reaction.

After the completion of the reaction, the obtained reaction product was diluted 20-fold with water and analyzed by high-performance liquid chromatography (HPLC, Agilent; equipped with a carbohydrate column). The yield of the isosorbide produced was 36.0 mol % (28.9 wt %).

Example 2

The procedure of Example 1 was repeated, except that the reaction was performed with stirring at 190° C. for 6 hours. The yield of isosorbide produced was 40.9 mol % (32.8 wt %).

Example 3

The procedure of Example 1 was repeated, except that the reaction was performed with stirring at 200° C. for 7 hours. The yield of isosorbide produced was 66.7 mol % (53.5 wt %).

Example 4

The procedure of Example 3 was repeated, except that 6.05 mmol (1.75 parts by mole based on 100 parts by mole of D-sorbitol contained in the reactant) of the naphthalenesulfonic acid catalyst was added. The yield of isosorbide produced was 73.2 mol % (58.7 wt %).

Example 5

The procedure of Example 1 was repeated, except that the reaction was performed with stirring at 220° C. for 7 hours. The yield of isosorbide produced was 73.8 mol % (59.2 wt %).

Example 6

The procedure of Example 1 was repeated, except that 6.05 mmol (1.75 parts by mole based on 100 parts by mole of D-sorbitol contained in the reactant) of the naphthalenesulfonic acid catalyst was added and that the reaction was performed at 220° C. for 4 hours. The yield of isosorbide produced was 78.7 mol % (63.1 wt %).

Example 7

The procedure of Example 5 was repeated, except that the reaction was performed with stirring at 230° C. for 4 hours. The yield of isosorbide produced was 73.8 mol % (59.2 wt %).

Example 8

A reactant comprising 5 wt % of ethanol, 25 wt % of distilled water and 70 wt % of D-sorbitol was prepared. 90 g of the reactant, which contains 63 g (0.3458 mol) of D-sorbitol, and 6.05 mmol (1.75 parts by mole based on 100 parts by mole of D-sorbitol contained in the reactant) of a naphthalenesulfonic acid catalyst, were introduced into an autoclave reactor and allowed to react with stirring at 220° C. for 5 hours. Because the reaction pressure used was autogenous pressure, the reaction pressure showed a slight different between the initial stage of the reaction and the end stage of the reaction depending to the degree of progress of the reaction.

After the completion of the reaction, the obtained reaction product was diluted 20-fold with water and analyzed by high-performance liquid chromatography. The yield of the isosorbide produced was 68.8 mol % (55.2 wt %). Meanwhile, the amount of carbide attached to the reactor surface and the impeller decreased by about 40% compared to that in Example 6.

Example 9

The procedure of Example 1 was repeated, except that 6.05 mmol (1.75 parts by mole based on 100 parts by mole of D-sorbitol contained in the reactant) of the methanesulfonic acid catalyst was added and that the reaction was performed at 230° C. for 3.5 hours. The yield of isosorbide produced was 62.9 mol % (49.5 wt %).

Example 10

The procedure of Example 1 was repeated, except that 6.05 mmol (1.75 parts by mole based on 100 parts by mole of D-sorbitol contained in the reactant) of the p-toluenesulfonic acid catalyst was added and that the reaction was performed at 220° C. for 4 hours. The yield of isosorbide produced was 70.2 mol % (55.9 wt %).

Comparative Example 1

Isosorbide was produced according to the method disclosed in Example 2 of U.S. Pat. No. 7,420,067. Specifically, sorbitol (37.78 g) was dissolved in water (500 ml) and transferred to a 1-L autoclave reactor vessel. The catalyst, calcined CBV 3024E (Zeolyst International, 7.55 g), was added and after flushing the reactor three times with hydrogen, pressure was set to 500 psi (34.47 bar). The reactor was heated, with stirring, to 280° C., over a time period of about 30 to about 45 minutes. After 15 minutes at 280° C., the yield of isosorbide was 51.4 mo % (41.2 wt %).

Comparative Example 2

Isosorbide was produced according to the method disclosed in Example 1 of U.S. Pat. No. 6,013,812. Specifically, 8 kg of D-sorbitol in the form of a 50 wt % solution in water was introduced into a 1-L autoclave reactor. 5 wt % of propionic acid and 1 wt % of a Pd/C catalyst (Pd content: 3 wt %) were added thereto. The reaction mixture was heated to 270° C. and stirred for 2 hours at a $H_2$ pressure of 60 bar. After cooling, the catalyst was removed by filtration, and the water/catalyst mixture was removed by distillation. The yield of isosorbide produced was 38 mol % (30.5 wt %).

Comparative Example 3

The procedure of Example 1 was repeated, except that 6.05 mmol (1.75 parts by mole based on 100 parts by mole of D-sorbitol contained in the reactant) of sulfuric acid ($H_2SO_4$) was used as the catalyst and that the reaction was performed at 220° C. for 5 hours. The yield of isosorbide produced was 53.0 mo % (42.5 wt %).

Comparative Example 4

The procedure of Example 1 was repeated, except that 4.034 mmol (1.166 parts by mole based on 100 parts by mole of D-sorbitol contained in the reactant) of sulfuric acid ($H_2SO_4$) and 2.016 mmol (0.584 parts by mole based on 100 parts by mole of D-sorbitol contained in the reactant) of naphthalenesulfonic acid were used as the catalyst and that the reaction was performed at 220° C. for 5 hours. The yield of isosorbide produced was 60.7 mol % (48.7 wt %).

The yield of the product obtained in each of Examples 1 to 8 and Comparative Examples 1 to 4 was calculated using the following equation, and the results of the calculation are shown in Table 1 below.

mol % yield=number of moles of isosorbide produced/number of moles of sorbitol introduced×100 wt % yield=weight of isosorbide produced/weight of sorbitol introduced×100

TABLE 1

| | Temp. (° C.) | Pressure (bar) | Catalyst | Reaction time | Yield of isosorbide mol % | Yield of isosorbide wt % |
|---|---|---|---|---|---|---|
| Example 1 | 180 | 10-13 | 0.875 parts by mole of NSA | 8 hr | 36.0 | 28.9 |
| Example 2 | 190 | 12-15 | 0.875 parts by mole of NSA | 6 hr | 40.9 | 32.8 |
| Example 3 | 200 | 14-20 | 0.875 parts by mole of NSA | 7 hr | 66.7 | 53.5 |
| Example 4 | 200 | 14-20 | 1.75 parts by mole of NSA | 7 hr | 73.2 | 58.7 |
| Example 5 | 220 | 22-30 | 0.875 parts by mole of NSA | 7 hr | 73.8 | 59.2 |
| Example 6 | 220 | 22-30 | 1.75 parts by mole of NSA | 4 hr | 78.7 | 63.1 |
| Example 7 | 230 | 30-40 | 1.75 parts by mole of NSA | 4 hr | 73.8 | 59.2 |
| Example 8 | 220 | 30-37 | 1.75 parts by mole of NSA (solvent: ethanol + water) | 4 hr | 68.8 | 55.2 |
| Example 9 | 230 | 25-31 | 1.75 parts by mole of MSA | 3.5 hr | 62.9 | 49.5 |
| Example 10 | 220 | 21-22 | 1.75 parts by mole of PTSA | 4 hr | 70.2 | 55.9 |
| Comp. Ex. 1 | 280 | 34.47 | Acidic zeolite | 45 min-1 hr | 51.4 | 41.2 |
| Comp. Ex. 2 | 270 | 60 | propionic acid | 2 hr | 38 | 30.5 |
| Comp. Ex. 3 | 220 | 20-25 | 1.75 parts by mole of sulfuric acid | 5 hr | 53.0 | 42.5 |
| Comp. Ex. 4 | 220 | 20-25 | Mixture of 1.166 parts by mole of sulfuric acid and 0.584 parts by mole of NSA | 5 hr | 60.7 | 48.7 |

As shown in Table 1 above, the yield of isosorbide produced in Examples 1 to 10 by performing the high-temperature and high-pressure reaction using the catalyst according to the present invention reached an isosorbide yield of up to 78.7 mol % (63.1 wt %), which is equal to that of a conventional vacuum reaction performed using a sulfuric acid catalyst.

INDUSTRIAL APPLICABILITY

As described above, the method of preparing anhydrosugar alcohol according to the present invention can achieve an anhydrosugar alcohol yield similar to that of a vacuum reaction, and does not need to be maintained at a high vacuum level. Thus, the method of the present invention makes it possible to reduce the operating cost of the reaction and the equipment cost of the reactor.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing anhydrosugar alcohol, the method comprises:
dehydrating a sugar alcohol at a pressure of 10 bar to 50 bar in a presence of a catalyst,
wherein the catalyst is naphthalenesulfonic acid.

2. The method of claim 1, wherein the dehydration is performed at a temperature of 160° C. to 260° C.

3. The method of claim 1, wherein the anhydrosugar alcohol is isosorbide, and the sugar alcohol is sorbitol.

4. The method of claim 1, which is performed in a continuous stirred tank reactor (CSTR), a plug flow reactor (PFR) or a batch reactor (BR).

5. The method of claim 1, wherein water, ethanol or a mixture thereof is used as a solvent.

6. The method of claim 1, wherein the dehydration is performed in a plug flow reactor.

7. The method of claim 1, wherein the catalyst further comprises sulfuric acid.

8. A method of preparing anhydrosugar alcohol, the method comprises:
dehydrating a sugar alcohol at a pressure of 10 bar to 50 bar in a presence of a catalyst, wherein the catalyst is at least one of methanesulfonic acid and p-toluenesulfonic acid.

9. The method of claim 8, wherein the catalyst is methanesulfonic acid.

10. The method of claim 8, wherein the catalyst is p-toluenesulfonic acid.

11. The method of claim 8, wherein the dehydration is performed at a temperature of 160° C. to 260° C.

12. The method of claim 8, wherein the anhydrosugar alcohol is isosorbide, and the sugar alcohol is sorbitol.

13. The method of claim 8, which is performed in a continuous stirred tank reactor (CSTR), a plug flow reactor (PFR) or a batch reactor (BR).

14. The method of claim 8, wherein water, ethanol or a mixture thereof is used as a solvent.

15. The method of claim 8, wherein the dehydration is performed in a plug flow reactor.

* * * * *